Figure 1:
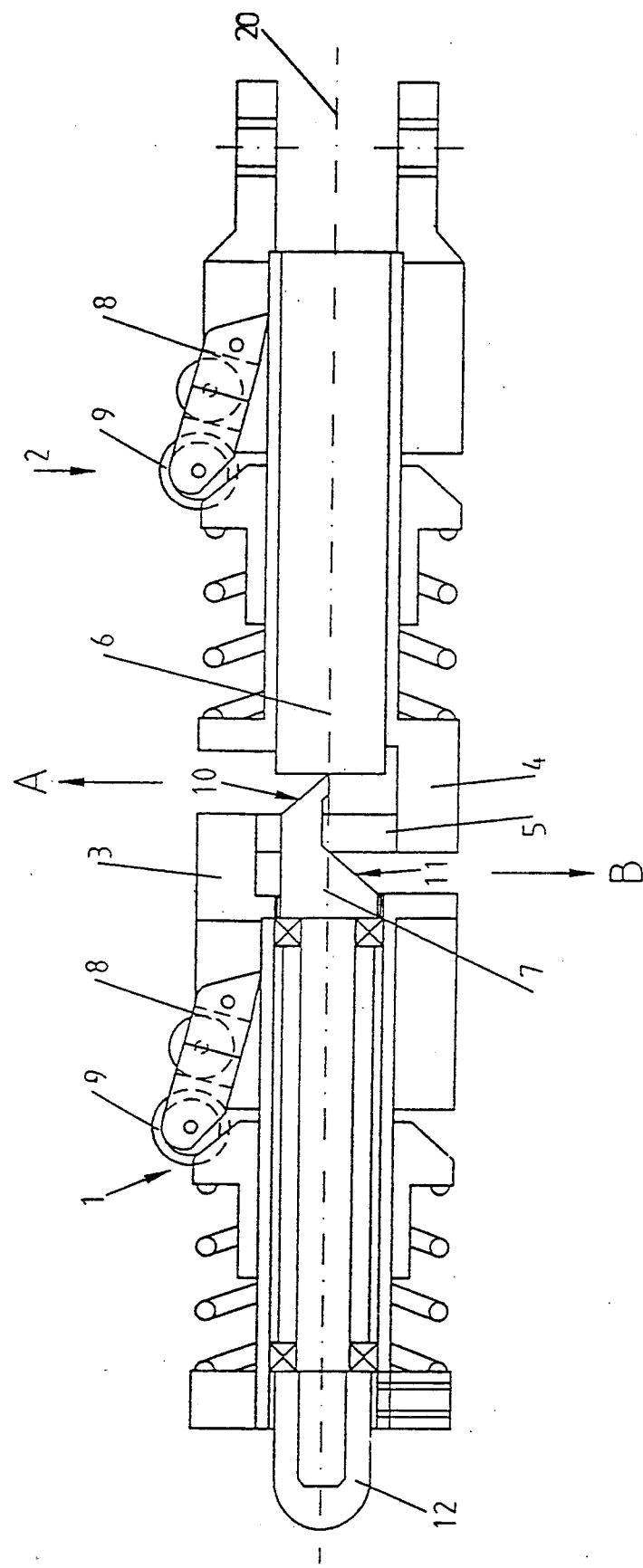

United States Patent [19]
Lodder et al.

[11] Patent Number: 5,099,692
[45] Date of Patent: Mar. 31, 1992

[54] APPARATUS FOR CARRYING MOBILE MEANS OF INSPECTION IN THE INTERIOR OF A TUBULAR BODY

[75] Inventors: Marten Lodder, Hilversum; Franciscus S. De Boer, Druten, both of Netherlands

[73] Assignee: Industrial Consultants Hoogovens BV, Diemen, Netherlands

[21] Appl. No.: 694,209

[22] Filed: May 3, 1991

[30] Foreign Application Priority Data

May 14, 1990 [NL] Netherlands ................. 9001124

[51] Int. Cl.$^5$ ............................................. G01N 29/04
[52] U.S. Cl. ............................... 73/623; 73/40.5 A
[58] Field of Search ............... 73/40.5 P, 622, 623, 73/627, 637, 638, 640, 644, 1 DV, 865.8, 866.5

[56] References Cited

U.S. PATENT DOCUMENTS 4,361,044 11/1982 Kupperman et al. ................ 73/623

FOREIGN PATENT DOCUMENTS 0078072 5/1983 European Pat. Off. .
61-29759 2/1986 Japan .
7709083 3/1978 Netherlands ................. 73/623

Primary Examiner—Hezron E. Williams
Assistant Examiner—Shu-Cheng Kau
Attorney, Agent, or Firm—Stevens, Davis, Miller & Mosher

[57] ABSTRACT

An apparatus is provided for carrying a mobile inspection assembly in the interior of a tubular body, the assembly of inspection being adapted to emit and receive at least one sweeping radiation beam for inspection purposes. The apparatus includes a pair of carrier assemblies, coupled together by a bridge which has at least two linking pieces and a coupling piece therebetween. The apparatus also has a reflector with at least as many reflection planes as the bridge has linking pieces, each of which reflection planes defines a transmission path. The reflector is rotatable about a longitudinal axis through the carrier assemblies, the reflection planes being so arranged that at least one transmission path extends to the interior of the tubular body at any one time. Part of each transmission path is longitudinal and part is perpendicular to the longitudinal axis. The reflection planes are arranged so as to partially overlap.

4 Claims, 1 Drawing Sheet

APPARATUS FOR CARRYING MOBILE MEANS OF INSPECTION IN THE INTERIOR OF A TUBULAR BODY

BACKGROUND

The invention relates to an apparatus for carrying mobile means of inspection in the interior of a tubular body comprising: a first mobile carrier assembly; a second mobile carrier assembly and a bridge for coupling together the two carrier assemblies, which means of inspection are adapted to emit and receive at least one sweeping radiation beam for inspection purposes, and forming part of which means of inspection are a transducer which is arranged to adopt a stationary position in relation to the said carrier assemblies and is adapted to emit and receive the said radiation beam along a longitudinal imaginary axis through the carrier assemblies, and a reflector which is fitted at a predetermined distance from the said transducer and is rotatable in relation to the said longitudinal axis.

Such an apparatus is known from Dutch patent 181302. With such an apparatus ultrasonic sound is sent by the transducer in the direction of the reflector which comprises an inclined reflecting plane with which the radiation beam is sent in the direction of the interior of the tubular body to be inspected. The radiation beam reflected through the tubular body follows the same path but in the opposite direction and is detected by the transducer.

A problem of the known apparatus is that a circular and full detection on the interior of the tubular body is only possible in one recording pass by using at least two apparatuses in accordance with the known state of the art series-linked at a certain distance. Apart from the circumstances that this is a costly solution, it also gives rise to interference and a relative comparison of the measurement results of the series-linked apparatus in accordance with the known state of the art is not simple.

SUMMARY OF THE INVENTION

The object of the invention is to make possible an all-round recording on the interior of the tubular body using a single apparatus according to claim 1, whereby a reliable measurement is made available which has low susceptibility to interference.

To this end the apparatus in accordance with the invention is characterised in that the bridge for coupling together the carrier assemblies has at least two linking pieces adjacent to the longitudinal axis and extending longitudinally, as well as a coupling piece extending perpendicularly to the longitudinal axis for linking the said linking pieces, and in that the reflector has at least as many reflection planes as the bridge has linking pieces, each of which reflection planes defines a transmission path of which a part extends perpendicularly to the said longitudinal axis.

In a preferred embodiment of the invention the reflector is arranged in such a way that each of the reflecting planes is positioned at the level of a linking piece, so that as the reflector is rotated through 360° during operation, at least one transmission path extends up to the interior of the tubular body at any one time.

In a first embodiment of the reflector, two reflecting planes are used, each forming an angle of 45° relative to the longitudinal axis, whereby the said reflecting planes form an angle of 90° to each other. A preferred embodiment for this is one in which the reflecting surface located closest to the transducer partially overlaps the reflecting plane that is located behind it viewed in the longitudinal direction from the transducer. This prevents undesired reflections at the location of the reflecting plane lying behind.

Each carrier assembly is preferably centred in the tubular body to be inspected by a plurality of carrier arms. The carrier arms may have rolling elements attached thereto. There are preferably three such carrier arms around the circumference of each carrier assembly.

A non-limitative embodiment of the present invention will now be described in more detail with reference to the Figure.

SPECIFIC DESCRIPTION

The Figure shows an apparatus embodying the present invention for carrying mobile means of inspection in the interior of a tubular body. The apparatus has a first carrier assembly 1, a second carrier assembly 2 and a bridge comprising a linking piece 3 that is coupled to carrier assembly 1 and extends longitudinally on one side of the central longitudinal axis 20 of this carrier assembly; the bridge further comprises a linking piece 4 that is linked to carrier assembly 2 and that is placed on the opposite side of the longitudinal axis 20 and displaced relative to linking piece 3; finally the bridge comprises a coupling piece 5 for coupling linking pieces 3 and 4.

The apparatus is further provided with a transducer 6 which is incorporated in carrier assembly 2 and a reflector 7 which forms part of carrier assembly 1. Each carrier assembly 1, 2 is further provided with carrier arms 8 onto which rolling elements 9 are attached, there being three of the carrier arms 8 around the circumference of the respective carrier assemblies for centring the two carrier assemblies 1, 2 in the tubular body to be inspected.

Reflector 7 comprises two reflecting planes 10, 11. Reflecting plane 10 is positioned at the level of linking piece 4 and defines a transmission path that extends partly in the direction of arrow A perpendicular to the longitudinal axis 20 of the apparatus. The reflecting plane 11 lying behind reflecting plane 10 in the direction of the longitudinal axis 20 from the transducer 6 defines a further transmission path which extends at least partly in the direction of arrow B perpendicular to the longitudinal axis 20. The reflecting plane 11 partially overlaps the reflecting plane 10.

During operation of the apparatus, the reflector 7 is rotated by motor 12 about the longitudinal axis and the respective transmission paths defined by reflection planes 10 and 11 rotate in such a way that at least one transmission path extends to the interior of the tubular body to be inspected at any one time.

The apparatus in accordance with the invention is suitable for applications including inspecting the wall thickness of the tubular body, and for inspecting for cracks in it.

What is claimed is:

1. An apparatus for carrying mobile means of inspection in the interior of a tubular body, which means of inspection are adapted to emit and receive at least one sweeping radiation beam for inspection purposes, and forming part of which means of inspection is a transducer which is adapted to emit and receive said radiation beam longitudinally, the apparatus comprising;
 (a) a first mobile carrier assembly;
 (b) a second mobile carrier assembly;
 (c) a longitudinal axis through the mobile carrier assemblies;
 (d) a bridge for coupling together the first and second carrier assemblies, and
 (e) a reflector which is arranged to be at a predetermined distance from the said transducer and is rotatable in relation to said longitudinal axis, wherein the carrier assemblies are arranged to adopt a stationary position in relation to the transducer, and the bridge for coupling together the carrier assemblies has at least two linking pieces adjacent to the longitudinal axis and extending longitudinally, as well as a coupling piece extending perpendicularly to the longitudinal axis for linking said linking pieces, and said reflector has at least as many reflection planes as the bridge has linking pieces, wherein each of which reflection planes defines a transmission path of which a part extends perpendicularly to the said longitudinal axis.

2. Apparatus according to claim 1 wherein the reflector is arranged in such a way that each of the reflecting planes is positioned at a corresponding level of a linking piece, at least one transmission path extending to the interior of the tubular body at any one time at any position of the reflector in rotation about the longitudinal axis.

3. Apparatus according to claim 1 wherein the reflecting plane which is located closest to the transducer slightly overlaps the reflecting plane which is located behind it as viewed in the longitudinal direction from the position of the transducer.

4. Apparatus according to claim 2 wherein the reflecting plane which is located closest to the transducer slightly overlaps the reflecting plane which is located behind it as viewed in the longitudinal direction from the position of the transducer.

* * * * *